United States Patent
Bennett

(10) Patent No.: US 6,399,832 B1
(45) Date of Patent: Jun. 4, 2002

(54) PROCESS FOR PRODUCING ORGANIC TRISULFIDES

(75) Inventor: Brooks D. Bennett, Borger, TX (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/607,559

(22) Filed: Jun. 29, 2000

(51) Int. Cl.$^7$ .............................................. C07C 321/00
(52) U.S. Cl. .......................................... 568/26; 568/25
(58) Field of Search ............................. 568/21, 25, 26

(56) References Cited

U.S. PATENT DOCUMENTS

| | | | | |
|---|---|---|---|---|
| 5,146,000 A | * | 9/1992 | Ozbalik | 568/26 |
| 5,155,275 A | | 10/1992 | Shaw | 568/21 |
| 5,232,623 A | | 8/1993 | Shaw | 252/183.13 |
| 5,442,123 A | | 8/1995 | Arretz et al. | 568/26 |
| 5,530,163 A | | 6/1996 | Shaw | 568/26 |
| 5,861,539 A | * | 1/1999 | Shaw | 568/26 |
| 5,907,064 A | | 5/1999 | Shaw | 568/21 |
| 6,051,739 A | * | 4/2000 | Shaw | 568/26 |

OTHER PUBLICATIONS

CA:100:51051 abs of Bull Chem Soc Jpn by Akiyama 56(9) pp. 2657–60 1983.*

"Hawley's Condensed Chemical Dictionary "12th Edition Revised by Richard J Lewis Sr p. 304 Van Nostrand Reinhold Publishers, New York 1993.*

* cited by examiner

*Primary Examiner*—Jean F. Vollano
(74) *Attorney, Agent, or Firm*—Charles W. Stewart

(57) ABSTRACT

Selectively producing organic trisulfides by contacting a mercaptan, a sulfur compound, and a catalyst under conditions sufficient to produce a reaction product comprising organic polysulfides, and subjecting the reaction product to trisulfide enhancing conditions which are effective to inhibit the formation of organic disulfides and promote the conversion of organic tetrasulfides to organic trisulfides.

32 Claims, No Drawings

PROCESS FOR PRODUCING ORGANIC TRISULFIDES

The present invention relates to a process for selectively producing organic trisulfides.

BACKGROUND OF THE INVENTION

Organic polysulfides, especially organic trisulfides, are useful for many purposes such as additives for elastomers, antioxidants for lubricating oils, intermediates for the production of organic chemicals, insecticides, and germicides, and additives for diesel fuels to improve cetane number and ignition qualities. Organic polysulfides are also useful in the compounding of high pressure lubricants and in the acceleration of rubber treating processes.

It is known that organic polysulfides can be produced by reacting mercaptans with elemental sulfur in the presence of a catalyst. The product of such reaction typically comprises a distribution of individual organic polysulfide compositions, each containing a different number of sulfur atoms. In many commercial applications, especially for use in high pressure lubricants, organic trisulfides exhibit more desirable properties than other organic polysulfides. For example, organic polysulfides containing more than three sulfur atoms exhibit high copper-strip corrosivity (ASTM Copper Strip Corrosion Test D-130-56), rendering them unsatisfactory for many commercial applications. In addition, organic disulfides can be undesirable because they have a high flash point and exhibit poor lubrication properties.

If an organic polysulfide product contains a high quantity of organic polysulfides having more or less than three sulfur atoms, costly separation processes and equipment can be necessary to remove undesirable polysulfides and recover a more pure organic trisulfide product that is suitable for commercial purposes. Therefore, a reaction product having a distribution of organic polysulfides which maximizes the amount of organic trisulfides while minimizing the amount of other organic polysulfides is desired.

Conventional processes for making high-purity organic trisulfides typically require expensive catalysts and multiple reaction vessels, both of which contribute to the expense of the overall process.

In addition, conventional processes for making high-purity organic trisulfides typically require the mercaptan-sulfur reaction to be terminated before substantial completion in order to avoid the formation of undesirable organic polysulfides in the reaction product. Terminating the mercaptan/sulfur reaction before it goes to substantial completion causes the presence of unreacted mercaptan and/or sulfur in the reaction product. Such unreacted mercaptan and/or sulfur must be removed from the reaction product, thus requiring additional costly separation processes and equipment.

SUMMARY OF THE INVENTION

An object of the present invention is to provide a process for selectively producing organic trisulfides.

Another object of the inventive process is to provide an organic polysulfide product having a higher concentration of organic trisulfides than products from conventional processes for making organic polysulfides.

A further object of the inventive process is to provide an organic polysulfide product having a lower concentration of organic tetrasulfides than products from conventional processes for making organic polysulfides.

A still further object of the inventive process is to provide an organic polysulfide product having a lower concentration of organic disulfides than products from conventional processes for making organic polysulfides.

An even further object of the present invention is to eliminate the need for expensive processes and equipment necessary to separate and recover a substantially pure organic trisulfide product.

A still further object of the inventive process is to eliminate the need for expensive catalysts which are required by conventional methods of selectively producing organic trisulfides.

Other objects and advantages of the present invention will become more apparent as the invention is more fully disclosed hereinbelow.

According to an embodiment of the present invention, a process for the selective production of organic trisulfides is provided. The process comprises contacting a mercaptan, a sulfur compound, and a catalyst in a reaction vessel under reaction conditions sufficient to produce a reaction product comprising an organic polysulfide product and subjecting the reaction product to trisulfide enhancing conditions which are effective to inhibit the formation of organic disulfides and promote the conversion of organic tetrasulfides to organic trisulfides.

In another embodiment of the present invention a process for selectively producing organic trisulfides is provided. The process comprises (a) contacting a mercaptan, a sulfur compound, and a catalyst in a reaction vessel under reaction conditions sufficient to produce a reaction product comprising an organic polysulfide product and hydrogen sulfide, thereby creating within the reaction vessel a liquid reaction solution comprising a mixture of liquid phase compounds, wherein a liquid hydrogen sulfide concentration is present in the liquid reaction solution; (b) increasing, for an initial reaction period, the liquid hydrogen sulfide concentration to a disulfide inhibiting hydrogen sulfide concentration that is effective to inhibit the formation of organic disulfides within the liquid reaction solution; (c) maintaining the disulfide inhibiting hydrogen sulfide concentration for a final reaction period; (d) lowering the temperature and pressure in the reaction vessel to trisulfide enhancing conditions that are effective to inhibit the formation of organic disulfides and promote the conversion of organic tetrasulfides to organic trisulfides; and (e) maintaining the trisulfide enhancing conditions within the reaction vessel for a trisulfide enhancing period.

DETAILED DESCRIPTION OF THE INVENTION

It has been discovered that, in a process for making organic polysulfides by reacting a mercaptan and a sulfur compound, the relative amount of organic trisulfides to other organic polysulfides in the reaction product can be increased by subjecting the product of the mercaptan/sulfuir reaction to trisulfide enhancing conditions.

The process of the present invention can be commenced by contacting a mercaptan, a sulfur compound, and a catalyst in a suitable reaction vessel to create a "liquid reaction solution" in the reaction vessel. The contacting of the mercaptan, sulfur compound and catalyst is generally accomplished by slowly adding one of the reactants to a mixture of the other reactant and the catalyst.

As used herein, the term "liquid reaction solution" means a mixture of all liquid phase compounds present in a reaction vessel. The composition of the liquid reaction solution of the present invention changes as the process progresses, however, during at least a portion of the process the liquid reaction solution can comprise unreacted mercaptan, the catalyst, organic polysulfides, and hydrogen sulfide.

The mercaptan suitable for use as a reactant in the process of the present invention can be any mercaptan having the formula of RSH, wherein R is a hydrocarbyl radical having 1 to about 30, preferably about 1 to about 20, and most preferably 2 to 15 carbon atoms. The hydrocarbyl radical can be linear or branched and can be alkyl, aryl, cycloalkyl, alkylaryl, aralkyl, alkenyl radicals, or combinations of two or more thereof. Preferably the hydrocarbyl radical is an alkyl radical. Presently preferred mercaptans are tertiary mercaptans. The presently most preferred mercaptan is t-butyl mercaptan.

The sulfur compound suitable for use as a reactant in the process of the present invention can be any sulfur containing compound capable of reacting with a mercaptan to produce an organic trisulfide and hydrogen sulfide. Preferably the sulfur compound is elemental sulfur.

The amount of sulfur compound contacted with the mercaptan depends on the desired sulfur content of the organic polysulfide product. For an average sulfur content of q sulfurs per polysulfide molecule, (q-1) moles of sulfur must be added per 2 moles of mercaptan and 1 mole of hydrogen sulfide will be produced per 2 moles of mercaptans reacted. It is, however, preferred that about 0.5 to about 10, preferably about 1.0 to about 5, and most preferably 1.0 to 2.0 moles of mercaptan per mole of sulfur is used.

The catalyst suitable for use in the process of the present invention can be any catalyst capable of catalyzing the reaction of a mercaptan and a sulfur compound to form hydrogen sulfide and an organic trisulfide. The presently preferred catalyst comprises a basic catalyst which can be an inorganic base, an organic base, or combinations of two or more thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, trimethylamine, triethylamine, n-butylamine and combinations of two or more thereof. Suitable inorganic bases include, but are not limited to, lithium hydroxide, sodium hydroxide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R_1ONa$, $R_1SNa$, and combinations of any two or more thereof; where $R_1$ is a $C_1$–$C_{18}$ alkyl radical, or combinations of any two or more thereof. Presently, the amine catalysts are not as preferred as other catalysts, and an inorganic base is preferred because of the availability and low cost of inorganic bases. Among the inorganic bases, sodium hydroxide is preferred because it is readily available and inexpensive.

The catalyst useful in the process of the present invention can further comprise an alkoxylated compound, preferably and alkoxylated alcohol. The alkoxylated alcohol useful in the present invention has a general formula of $R_2O[CH_2CH(R_3)O]_mH$ where $R_2$ is a $C_1$–$C_{20}$ hydrocarbyl radical selected from the group consisting of alkyl radical, alkylaryl radical, aryl radical, cycloalkyl radical and alkenyl radical. Preferably $R_2$ is a $C_6$–$C_{18}$ alkyl radical. Most preferably $R_2$ is a $C_{10}$–$C_{16}$ alkyl radical. Preferably $R_3$ is selected from the group consisting of hydrogen, $C_1$–$C_6$ alkyl radicals, and $C_2$–$C_{16}$ alkenyl radicals. Preferably $R_3$ is a hydrogen or a $C_1$–$C_3$ alkyl radical. Most preferably $R_3$ is hydrogen. Preferably m is a number from 1 to about 20, more preferably from about 2 to about 12, and most preferably from 5 to 10. An example of a suitable alkoxylated alcohol is TERGITOL® 15-S-7 which is an ethoxylated alcohol, manufactured and marketed by Union Carbide Corporation, and having the formula of $R_2O(CH_2 CH_2O)_7H$ where $R_2$ is a secondary alkyl radical having 11–15 carbon atoms and 7 is the average number of the ethylene oxide units. Another example is an ethoxylated phenol having the same number of ethylene oxide units. Other suitable alkoxylated alcohols are also available from Union Carbide Corporation.

The weight ratio of base to alkoxylated compound in the catalyst can vary widely so long as the ratio can catalyze the reaction of a mercaptan and a sulfur compound. Preferably the weight ratio of a base to an alkoxylated compound is from about 10:1 to about 1:100, more preferably from about 2:1 to about 1:10, most preferably from 1:1 to 1:5.

The amount of catalyst contacted with the mercaptan and sulfur compound of the present invention is any amount that can catalyze the formation of an organic polysulfide. The weight of the catalyst as a percentage of the weight of mercaptans can be in the range of from about 0.001 to about 10 percent, preferably from about 0.01 to about 3 percent, and most preferably from 0.05 to 2 percent.

The organic polysulfides produced by the reaction of a mercaptan and a sulfur compound can be any organic polysulfides having the formula of $RS_xR$, wherein each R can be the same or different and are each a hydrocarbyl radical having 1 to about 30, preferably 1 to about 20, and most preferably 2 to about 15 carbon atoms and x is a number from 2 to about 10, preferably 2 to 6, more preferably 3 to 5, and most preferably 3. The hydrocarbyl radical can be linear or branched and can be alkyl, aryl, cycloalkyl, alkylaryl, aralkyl, alkenyl radicals, or combinations of two or more thereof. Preferably the hydrocarbyl radical is an alkyl radical. Preferred organic polysulfides are di-t-butyl polysulfides. The most preferred organic polysulfide is di-t-butyl trisulfide.

In accordance with an embodiment of the present invention, during a reaction period, reaction conditions are employed which facilitate the reaction of the mercaptan and sulfur compound. The reaction period can commence with the commencement of the mercaptan/sulfur reaction and terminate when the mercaptan/sulfur reaction is substantially complete. The mercaptan/sulfur reaction is substantially complete when substantially all of the sulfur compound originally charged to the reaction vessel has been consumed. Preferably, the mercaptan/sulfur reaction is substantially complete when the weight of the sulfur compound present in the reaction vessel as a percentage of the weight of the sulfur compound originally charged to the reaction vessel is less than about 20 percent, more preferably less than about 10 percent, and most preferably less than 5 percent. The reaction period can be from about 0.5 to about 20 hours, more preferably from 1 to 10 hours.

The conditions employed during the reaction period typically include elevated temperatures and variable pressures. Stirring of the liquid reaction solution can also be employed to accelerate the mercaptan/sulfur reaction. The temperature employed during the reaction period is preferably from about 50° C. to about 150° C., more preferably from about 80° C. to about 130° C., and most preferably from 95° C. to 115° C.

The reaction period preferably comprises an initial reaction period and a final reaction period. The initial reaction period can commence with the commencement of the mercaptan/sulfur reaction and terminate when the amount of hydrogen sulfide in the liquid reaction solution reaches a "disulfide inhibiting hydrogen sulfide concentration". The "disulfide inhibiting hydrogen sulfide concentration" is preferably such that the weight of liquid hydrogen sulfide as a percentage of the total weight of the liquid reaction solution is from about 0.1 percent to about 10 percent, more preferably from about 0.3 percent to about 5 percent, still more preferably from about 0.5 percent to about 2 percent, and most preferably from 0.8 percent to 1.5 percent.

When the mercaptan and sulfur compound react, hydrogen sulfide evolves. During the initial reaction period, it may be necessary to vent gaseous hydrogen sulfide from the reaction vessel in order to prevent undesirably high pressures within the reaction vessel. However, the method of venting hydrogen sulfide from the reaction vessel preferably employs a venting rate which allows for the concentration of hydrogen sulfide in the liquid reaction solution to increase during the initial reaction period. Preferably, during the initial reaction period, the hydrogen sulfide concentration in the liquid reaction solution increases from essentially zero to the disulfide inhibiting hydrogen sulfide concentration. The increase in hydrogen sulfide concentration in the liquid reaction solution can be caused by adding hydrogen sulfide to the liquid reaction solution from an external source and/or by utilizing the hydrogen sulfide which evolves in-situ, via the mercaptan/sulfur reaction. Preferably, the hydrogen sulfide present in the liquid reaction solution is produced in-situ.

Although the disulfide inhibiting hydrogen sulfide concentration can be reached rapidly by employing a very slow rate of hydrogen sulfide venting during the initial reaction period, it is preferred in practicing the present invention for the rate of hydrogen sulfide venting during the initial reaction period to be such that the initial reaction period is sufficiently long to allow the majority (i.e., more than 50 wt.%) of the sulfur compound originally charged to the reaction vessel to be consumed. Preferably, the initial reaction period is sufficiently long to allow from about 50 weight percent to about 80 weight percent of the sulfur compound originally charged to the reaction vessel to be consumed. Most preferably, the initial reaction period is sufficiently long to allow from about 60 weight percent to about 75 weight percent of the sulfur compound originally charged to the reaction vessel to be consumed.

The reaction pressure during the initial reaction period can vary widely due to the evolving and venting of hydrogen sulfide. Preferably, the reaction pressure during the initial reaction period is from about 1 atmosphere to about 20 atmospheres, most preferably from about 1 atmosphere to about 10 atmospheres.

The initial reaction period can be from about 0.2 hours to about 10 20 hours, preferably from about 0.5 hours to about 8 hours, and most preferably from 1 hour to 3 hours.

After the initial reaction period, the amount of hydrogen sulfide in the liquid reaction solution is preferably maintained at a disulfide inhibiting hydrogen sulfide concentration for a final reaction period. The final reaction period can commence when the amount of hydrogen sulfide in a liquid reaction solution reaches the disulfide inhibiting hydrogen sulfide concentration and terminate when the mercaptan/sulfur reaction is substantially complete. The mercaptan/sulfur reaction is substantially complete when substantially all of the sulfur compound originally charged to the reaction vessel has been consumed. Preferably, the mercaptan/sulfur reaction is substantially complete when the weight of the sulfur compound in the reaction vessel as a percentage of the original weight of the sulfur compound charged to the reaction vessel is less than about 20 percent, more preferably less than about 10 percent, and most preferably less than 5 percent.

The disulfide inhibiting hydrogen sulfide concentration maintained during the final reaction period can be maintained by any method known in the art. Preferably, the disulfide inhibiting hydrogen sulfide concentration is maintained by slowing and/or terminating the release of hydrogen sulfide from the reaction vessel. Most preferably, the disulfide inhibiting hydrogen sulfide concentration is maintained by sealing the reaction vessel during the final reaction period, thereby trapping the hydrogen sulfide in the reaction vessel.

The reaction pressure during the final reaction period is typically from about 1 atmosphere to about 10 atmospheres, more typically from about 1 atmosphere to about 5 atmospheres.

The final reaction period can be from about 0.1 hours to about hours, preferably from about 0.2 hours to about 5 hours, and most preferably from 0.5 hours to 2 hours.

After the final reaction period, the conditions within the reaction vessel are changed from the final reaction conditions to "trisulfide enhancing conditions". The transition between final reaction conditions and trisulfide enhancing conditions preferably takes place during a relatively short transition period. Preferably, such transition period is less than 1 hour, more preferably less 0.5 hours, and most preferably less than 0.25 hours.

During the transition period, it is preferred for the temperature within the reaction vessel to be reduced from the final reaction temperature to a "trisulfide enhancing temperature". The trisulfide enhancing temperature is preferably less than about 90 percent, more preferably less than about 70 percent, and most preferably less than 60 percent of the final reaction temperature. The trisulfide enhancing temperature is preferably from about 10° C. to about 80° C., more preferably from about 25 ° C. to about 65° C., and most preferably from 40° C. to 50° C.

During the transition period, it is preferred for the pressure in the reaction vessel to be reduced from the reaction pressure to a "trisulfide enhancing pressure". The trisulfide enhancing pressure is preferably less than about 50, more preferably less than about 25 percent, and most preferably less than 10 percent of the final reaction pressure. The trisulfide enhancing pressure can be from about −150 psig to about 25 psig, preferably from about −50 psig to about 10 psig, more preferably the trisulfide enhancing pressure is less than 0 psig, even more preferably from about −10 psig to about −1 psig, and most preferably from −5 psig to −2 psig.

During the transition period, it is preferred for the concentration of hydrogen sulfide within the liquid reaction solution to be decreased from the disulfide inhibiting hydrogen sulfide concentration to a "trisulfide enhancing hydrogen sulfide concentration". The trisulfide enhancing hydrogen sulfide concentration is preferably less than about 50 percent, more preferably less than about 20 percent, and most preferably less than 10 percent of the disulfide inhibiting hydrogen sulfide concentration. The trisulfide enhancing hydrogen sulfide concentration is preferably such that the weight of liquid hydrogen sulfide as a percentage of the total weight of all liquid phase compounds in the reaction product is less than about 5 percent, more preferably less than about 2 percent, and still more preferably less than about 1 percent, even more preferably less than about 0.5 percent, and most preferably less than 0.2 percent.

After the transition period, the reaction product is maintained at trisulfide enhancing conditions for a "trisulfide enhancing period". The trisulfide enhancing period can commence when trisulfide enhancing conditions are present in the reaction vessel and terminate when the organic polysulfide product has a "desired organic polysulfide distribution".

The trisulfide enhancing conditions maintained during the trisulfide enhancing period are preferably effective to inhibit the presence of organic disulfides and organic tetrasulfides in the organic polysulfide product. The amount of organic trisulfide in the organic polysulfide product is enhanced by employing conditions which promote the conversion of organic tetrasulfides to organic trisulfides while, at the same time, inhibiting the conversion of organic trisulfides to organic disulfides.

Trisulfide enhancing conditions typically include a low temperature, a low pressure, and a low concentration of hydrogen sulfide in the liquid reaction product. Preferably, the trisulfide enhancing temperature and pressure employed during the trisulfide enhancing period are sufficient to cause substantially all liquid hydrogen sulfide present in the liquid reaction solution to vaporize into gaseous hydrogen sulfide, thereby providing the trisulfide enhancing hydrogen sulfide concentration, described above.

The desired organic polysulfide distribution, which signals the end of the trisulfide enhancing period, is preferably indicated by an organic polysulfide product that has a weight percent of organic trisulfides that is greater than about 80 percent, more preferably greater than about 90 percent, even more preferably greater than about 95 percent, and most preferably greater than 97 percent of the total weight of the organic polysulfide product. The desired organic polysulfide product preferably has a weight ratio of organic trisulfides to organic disulfides which is greater than about 25:1, preferably greater than about 50:1, more preferably greater than about 80:1, and most preferably greater than about 95:1. The desired organic polysulfide product preferably has a weight ratio of organic trisulfides to organic tetrasulfides which is greater than about 25:1, preferably greater than about 50:1, more preferably greater than about 80:1, and most preferably greater than 95:1.

To determine when the liquid reaction solution contains an organic polysulfide product of desired organic polysulfide distribution, the composition of the liquid reaction product can be monitored during the tetrasulfide inhibiting reaction period. The concentration of the liquid reaction solution can be monitored by any method known in the art, for example by sampling and gas chromatograph analysis.

The trisulfide enhancing period can be from about 0.5 hours to about 20 hours, preferably from about 1 hour to about 10 hours, and most preferably from 2 hours to 4 hours.

After the trisulfide enhancing period, the reaction product can be contacted with carbon dioxide to provide a stable polysulfide product. As used herein, the term "stable" refers to product that does not substantially turn cloudy or hazy or increase in mercaptan content during the production or storage for at least 30 days, preferably 6 months. The term "substantially" means more than trivial.

The amount of carbon dioxide required to produce a stable product can be in the range of from about 0.1 to about 100,000, preferably about 0.5 to about 10,000, and most preferably 1 to 1,000 molar equivalent of the base used in the catalyst. The contacting of the product with carbon dioxide can be carried out under any conditions that are effective to produce a stable organic polysulfide product or can reduce susceptibility of the reaction product to decomposition during heating or sparging.

The residual hydrogen sulfide present in the product after the trisulfide enhancing period can be removed by venting. Removal of the residual hydrogen sulfide can take place either before or after contacting the liquid reaction solution with carbon dioxide to produce a stable product.

After residual hydrogen sulfide has been removed and the product has been stabilized, the unreacted mercaptan can be removed by any means known to one skilled in the art such as, for example, distillation and nitrogen sparging.

Further purification, separation, and recovery methods known to one skilled in the art can be used to recover a substantially pure organic polysulfide product.

The following examples are provided to further illustrate the practice of the present invention and are not intended to limit the scope of the invention of the claims.

EXAMPLE I

The following example demonstrates a non-inventive method of preparing organic polysulfides by reacting a mercaptan and a sulfur compound in the presence of a basic catalyst.

A 100 gallon Hastelloy C reactor (R-100) was initially charged with flour sulfur, sodium hydroxide, and ethoxylated alcohol (Union Carbide TERGITOL® 15-S-7) (see Table 1 for quantities). A 200 gallon Hastelloy C vessel (R-200) was charged with t-butyl mercaptan (see Table 1 for quantity). The mercaptan in R-200 was transferred to R-100 by pressurizing R-200 to 200 psig with nitrogen and opening a control valve located in the line connecting the two reactors. When all the mercaptan was transferred from R-200 to R-100 the control valve was closed. The transfer of mercaptan from R-200 to R-100 resulted in a pressure in R-100 of about 160 psig.

The agitator in R-100 was turned on, and the contents of R-100 were stirred for 10 minutes. The R-100 over head vent valve was opened slowly to reduce the pressure in R-100 to less than 5 psig. While the agitator was running, the contents of R-100 were heated to a temperature of 80° C. over a period of 20 minutes and held at that temperature for 10 minutes. While R-100 was heated to and maintained at 80° C., gaseous hydrogen sulfide was released through a restrictive orifice valve. The temperature in R-100 was then increased to and maintained at about 105° C. for a 2 hour initial reaction period, during which gaseous hydrogen sulfide was released through the restrictive orifice valve.

After the 2 hour initial reaction period, the concentration of hydrogen sulfide in the liquid reaction solution was between 0.5 and 2 weight percent. The venting of gaseous hydrogen sulfide through the restrictive orifice valve was then terminated in order to maintain a concentration of hydrogen sulfide in the liquid reaction solution of between 0.5 and 2 weight percent. The reaction vessel was sealed for a 1 hour final reaction period.

After the final reaction period the contents of R-100 were cooled to less than 45° C. and R-100 was vented to 0 psig. The contents of R-100 were then contacted with carbon dioxide to neutralize the basic catalyst. This caustic neutralization step was performed by pressurizing R-100 to 50 psia with carbon dioxide and turning on the roll pump in R-100 for 4 hours. After the roll pump was turned off, the contents of R-100 were cooled to 35° C. and R-100 was vented to less than 5 psig.

The bulk of the t-butyl mercaptan (TBM) was recovered by vacuum distillation. Residual TBM was then removed by nitrogen sparging leaving a di-t-butyl polysulfide product. The disulfides and tetrasulfides were then separated from the trisulfides by vacuum distillation.

Table 1 shows the distribution of di, tri, and tetrasulfides in the di-t-butyl polysulfide product for 3 runs employing the non-inventive process of this example.

TABLE 1

Non-inventive Process
No Post-Reaction Trisulfide Enhancing Period

| | Catalyst | | Reactants | | Distribution of Di-t-butyl Polysulfides | | |
|---|---|---|---|---|---|---|---|
| Run # | 50% NaOH (grams) | Tergitol (grams) | Sulfur (lbs) | TBM (lbs) | Disulfides (wt %) | Trisulfides (wt %) | Tetrasulfides (wt %) |
| 1 | 350 | 450 | 125 | 565 | 1.34 | 90.94 | 7.72 |
| 2 | 500 | 1450 | 100 | 450 | 1.17 | 93.22 | 5.61 |
| 3 | 300 | 1450 | 100 | 450 | 3.03 | 91.29 | 5.68 |
| | | | | Average | 1.85 | 91.81 | 6.34 |

EXAMPLE II

The following example demonstrates the inventive method of preparing polysulfides by reacting a mercaptan and sulfur in the presence of a basic catalyst and then exposing the reaction product to trisulfide enhancing conditions.

The inventive process was carried out using the same process steps employed in Example I, except, after the final reaction period, the temperature in the reaction vessel was reduced to about 50° C. and the pressure in R-100 was reduced to a vacuum pressure (see Table 2 for specific pressures). The low-pressure and low-temperature in R-100 caused substantially all liquid hydrogen sulfide in R-100 to vaporize. The low-pressure/low-temperature (i.e., "trisulfide enhancing") conditions were maintained in R-100 for a "trisulfide enhancing" period of 3 hours.

The product was then subjected to the neutralization and separation techniques described in Example I.

Table 2 shows the distribution of di, tri, and tetrasulfides in the di-t-butyl polysulfide product for 5 runs employing the inventive process of this example.

TABLE 2

Inventive Process
Employs Post-Reaction Trisulfide Enhancing Period

| | Catalyst | | Reactants | | "Trisulfide Enhancing" | Distribution of Di-t-butyl Polysulfides | | |
|---|---|---|---|---|---|---|---|---|
| Run # | 50% NaOH (grams) | Tergitol (grams) | Sulfur (lbs) | TBM (lbs) | Pressure (psig) | Disulfides (wt %) | Trisulfides (wt %) | Tetrasulfides (wt %) |
| 1 | 100 | 200 | 125 | 565 | −4.35 | 1.05 | 97.97 | 0.99 |
| 2 | 100 | 200 | 125 | 565 | −3.48 | 1.16 | 98.03 | 0.81 |
| 3 | 175 | 200 | 125 | 565 | −2.51 | 1.22 | 98.08 | 0.70 |
| 4 | 200 | 200 | 125 | 565 | −2.90 | 1.34 | 97.59 | 1.07 |
| 5 | 200 | 200 | 125 | 565 | −2.90 | 1.05 | 97.94 | 1.01 |
| | | | | | Average | 1.16 | 97.92 | 0.92 |

Table 2 shows that the inventive process is more selective towards di-t-butyl trisulfide than the non-inventive process. The inventive process increased trisulfide production by an average of 6.1 weight percent, decreased the amount of tetrasulfides in the polysulfide product by an average of about 5.4 weight percent, and decreased the amount of disulfides in the polysulfide product by an average of about 0.6 weight percent.

The specific examples herein disclosed are to be considered as being primarily illustrative. Various changes beyond those described will no doubt occur to those skilled in the art, and such changes are to be understood as forming a part of this invention insofar as they fall within the spirit and scope of the appended claims.

That which is claimed is:

1. A process for selectively producing organic trisulfides, said process comprises the steps of:

(a) contacting a liquid phase mercaptan, elemental sulfur and a catalyst in a reaction vessel to thereby form a liquid reaction solution, wherein said contacting is under reaction conditions which include a first reaction temperature exceeding about 50° C. and a first reaction pressure exceeding about one atmosphere and wherein said contacting is for a reaction period sufficient to produce a reaction product comprising an organic polysulfide product and hydrogen sulfide;

(b) maintaining during said reaction period a hydrogen sulfide concentration in said liquid reaction solution in the range of from about 0.1 percent to about 10 percent;

(c) after said reaction period, subjecting said reaction product to trisulfide enhancing conditions which include maintaining a trisulfide enhancing temperature and a trisulfide enhancing pressure for a trisulfide enhancing period sufficient to provide said organic polysulfide product of a desired distribution of organic polysulfides having a weight percent organic trisulfide greater than about 80 percent, and wherein said trisulfide enhancing temperature is less than about 80° C. and said trisulfide enhancing pressure is less than 0 psig; and (d) recovering said organic polysulfide product.

2. A process according to claim 1 wherein the trisulfide enhancing conditions employed during said trisulfide enhancing period are sufficient to vaporize substantially all said hydrogen sulfide present in said reaction product.

3. A process according to claim 2 wherein said organic polysulfide product has a desired distribution of organic polysulfides has a weight percent organo trisulfide greater than about 90 percent.

4. A process according to claim 3 wherein the trisulfide enhancing conditions employed during said trisulfide enhancing period are sufficient to maintain a concentration of hydrogen sulfide in said reaction vessel such that the weight of hydrogen sulfide as a percentage of the total weight of all compounds in said reaction vessel is less than about 5 percent.

5. A process according to claim 4 wherein said desired distribution of organic polysulfides includes (1) a weight percent of organic trisulfides that is greater than about 95 percent of the total weight of said organic polysulfide product, (2) a weight ratio of organic trisulfides to organic disulfides that is greater than about 25:1, and (3) a weight ratio of organic trisulfides to organic tetrasulfides that is greater than about 25:1.

6. A process according to claim 5 wherein said reaction period extends until the reaction of said mercaptan and said sulfur compound is substantially complete.

7. A process according to claim 6 wherein step (a) and step (c) take place in the same reaction vessel.

8. A process according to claim 1 wherein the trisulfide enhancing conditions employed during said trisulfide enhancing period are sufficient to maintain a concentration hydrogen sulfide in said reaction vessel such that the weight of hydrogen sulfide as a percentage of the total weight of all compounds in said reaction vessel is less than about 2 percent.

9. A process according to claim 8 wherein said desired distribution of organicpolysulfides includes (1) a weight percent of organic trisulfides that is greater than about 97 percent of the total weight of said organic polysulfide product, (2) a weight ratio of organic trisulfides to organic disulfides that is greater than about 50:1, and (3) a weight ratio of organic trisulfides to organic tetra sulfides that is greater than about 50:1.

10. A process according to claim 9 wherein said reaction period extends until the weight of elemental sulfur in said reaction vessel as a percentage of the weight of elemental sulfur compound originally charged to said reaction vessel is less than about 20 percent.

11. A process according to claim 10 wherein said first reaction temperature is from about 50° C. to about 150° C.

12. A process according to claim 11 wherein said catalyst is a basic catalyst.

13. A process according to claim 12 wherein said mercaptan has the formula of RSH, wherein R is a hydrocarbyl radical having 1 to 20 carbon atoms.

14. A process according to claim 13 wherein the trisulfide enhancing conditions employed during said trisulfide enhancing period are sufficient to maintain concentration of hydrogen sulfide in said reaction vessel such that the weight of hydrogen sulfide as a percentage of the total weight of all compounds in said reaction is less than about 1 percent.

15. A process according to claim 14 wherein said desired distribution of organic polysulfides includes (1) a weight percent of organic trisulfides that is greater than about 95 percent of the total weight of said organic polysulfide product, (2) a weight ratio of organic trisulfides to organic disulfides that is greater than about 80:1, and (3) a weight ratio of organic trisulfides to organic tetra sulfides that is greater than about 80:1.

16. A process according to claim 15 wherein said reaction period extends until the weight of elemental sulfur in said reaction vessel as a percentage of the weight of elemental sulfur originally charged to said reaction vessel is less than about 10 percent.

17. A process according to claim 16 wherein step (a) and step (c) take place in the same reaction vessel.

18. A process according to claim 1 wherein said trisulfide enhancing temperature is in the range of from about 10° C. to about 80° C.

19. A process according to claim 18 wherein said trisulfide enhancing pressure is in the range of from about −10 psig to about −1 psig.

20. A process according to claim 19 wherein said trisulfide enhancing period is from about 0.5 to about 20 hours.

21. A process according to claim 20 wherein said first reaction temperature is in the range of from about 80° C. to about 130° C.

22. A process according to claim 21 wherein said first reaction pressure is in the range of from about 0 psig to about 200 psig.

23. A process according to claim 22 wherein said reaction period is from about 0.5 to about 20 hours.

24. A process according to claim 23 wherein the trisulfide enhancing temperature is in the range of from about 25° C. to about 65° C.

25. A process according to claim 24 wherein the trisulfide enhancing pressure is in the range of from about −5 psig to about −2 psig.

26. A process according to 25 wherein said trisulfide enhancing period is from about 1 to about 10 hours.

27. A process according to claim 26 wherein said reaction period is from about 1 to about 10 hours.

28. A process according to claim 27 wherein said catalyst comprises a base and an alkoxylated compound.

29. A process according to claim 28 wherein said mercaptan has the formula of RSH, wherein R is a hydrocarbyl radical having 2 to 15 carbon atoms.

30. A process according to claim 29 wherein said catalyst comprises an inorganic base and an alkoxylated alcohol.

31. A process according to claim 30 wherein said mercaptan is a tertiary mercaptan.

32. A process according to claim 31 wherein step (a) and step (c) take place in the same reaction vessel.

* * * * *